United States Patent [19]

Fritsch

[11] Patent Number: 4,716,496
[45] Date of Patent: Dec. 29, 1987

[54] PANEL-MOUNTED CONTROL STATION HOUSING

[75] Inventor: Ronald J. Fritsch, Sussex, Wis.

[73] Assignee: Eaton Corporation, Cleveland, Ohio

[21] Appl. No.: 861,168

[22] Filed: May 9, 1986

[51] Int. Cl.$^4$ ............................................. H05K 7/00
[52] U.S. Cl. ..................................... 361/391; 174/48;
200/296; 220/3.8; 220/331; 248/27.1; 361/346
[58] Field of Search ................... 174/48, 58, 53, 65 R,
174/17 CT; 200/296; 220/3.8, 331, 329;
248/27.1; 361/346, 369, 370, 391

[56] References Cited
U.S. PATENT DOCUMENTS 2,183,372 12/1939 Thoma ............................... 248/27.1
2,746,635  5/1956 Ammon ............................. 248/27.1
3,549,828 12/1970 Lang ................................. 248/27.1

FOREIGN PATENT DOCUMENTS 0996330  6/1965 United Kingdom ............... 248/27.1

Primary Examiner—J. R. Scott
Assistant Examiner—Gregory D. Thompson
Attorney, Agent, or Firm—D. A. Rowe; L. G. Vande Zande

[57] ABSTRACT

A molded cover control station having transverse upper and lower grooves spaced apart by a distance less than the vertical dimension of a panel opening has a resilient gasket positioned against a rear flange, the gasket having a resilient protrusion which is received within the lower groove. Insertion of the control station housing from the rear of the panel such that the lower edge of the panel opening engages the resilient protrusion within the lower groove enables the resilient protrusion to be compressed an amount sufficient to enable the upper end of the housing to be swung forwardly through the opening to align the upper groove with an upper edge of the panel opening. The resiliency of the protrusion within the lower groove biases the housing upwardly to effect engagement between the upper groove and upper edge of the panel opening, and a screw carried by the housing is turned inwardly to project into the lower groove just above the lower edge of the panel opening to bear the weight of the control station and prevent the protrusion from being compressed.

14 Claims, 6 Drawing Figures

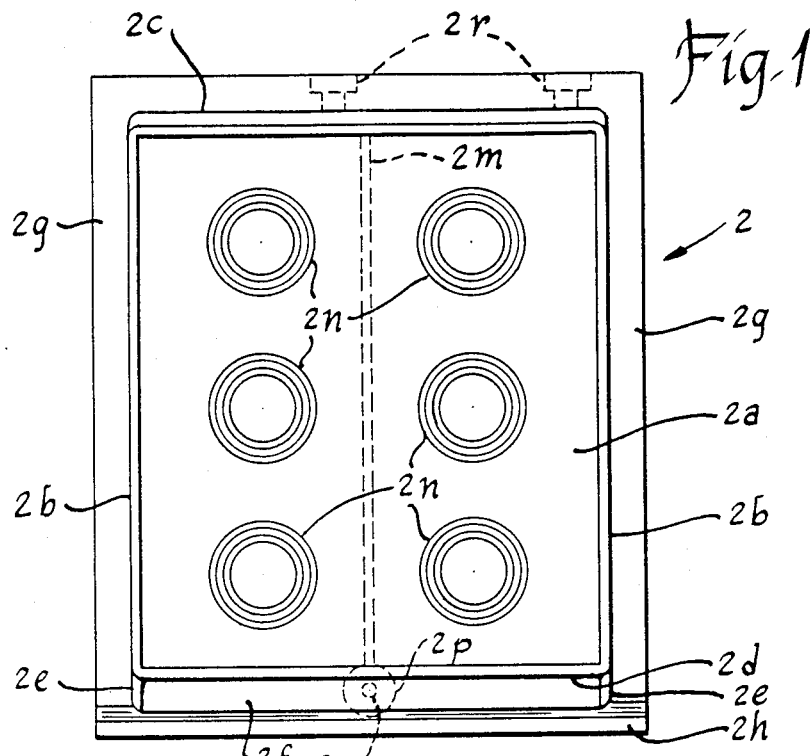
Fig. 1
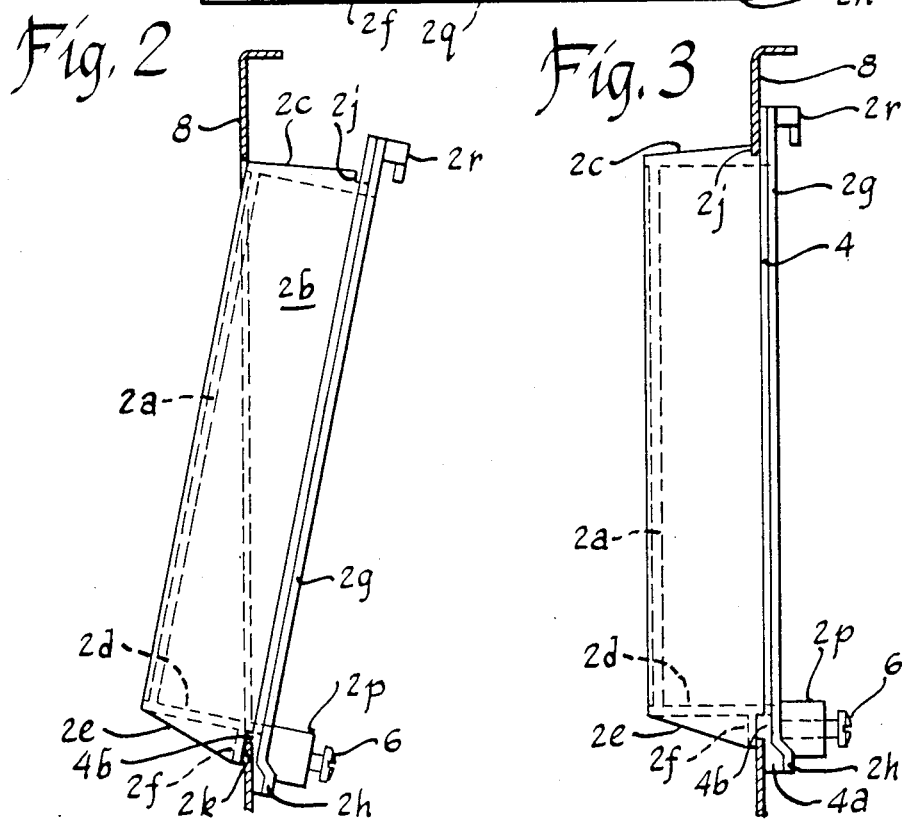
Fig. 2
Fig. 3

PANEL-MOUNTED CONTROL STATION HOUSING

BACKGROUND OF THE INVENTION

This invention relates to control stations used on enclosed electrical apparatus such as motor control centers. More particularly this invention pertains to a mounting structure for readily mounting or removing the control station housing to or from an exterior panel or door panel of the enclosure.

Motor control centers comprise a cabinet having a plurality of compartments closed by individual doors. Each compartment receives a removable motor control unit containing motor control apparatus such as manually operated circuit interrupters and/or electrically operated starters, reversers or the like. Manual operators for the circuit interrupters are fixed to the motor control unit and project through openings in the compartment door. Pilot control devices such as pushbuttons or rotary selector switches or the like for controlling the electrically operated apparatus are mounted to a control station, housing to comprise a control station which may also be affixed to the motor control unit to project through an opening in the door, or may be mounted to the door within the opening. The latter approach simplifies alignment and gasketing. However, the switches of the control station are wired to the control apparatus, therefore the control station must preferably be removable from the door to stay with the motor control unit when it becomes necessary to remove the motor control unit for testing or maintenance. It is desirable that such control stations, sometimes referred to as cover control or cover control islands, be attachable and removable quickly and with few simple operations.

SUMMARY OF THE INVENTION

This invention provides a control station housing which is readily mountable and demountable in an opening in a substantially vertically oriented panel, such as a flat surface panel of a door, by providing upper and lower grooves in a housing for the control station. The vertical distance between the bottoms of the respective grooves is less than the vertical dimension of the panel. The opening vertical dimension of the housing is greater than the vertical dimension of the panel opening. The lower groove contains a resilient member which is compressed upon insertion of the housing into the panel opening so that the lower groove engages the lower edge of the panel opening, thereby permitting the upper end of the housing to be pivoted through the panel opening to bring the upper groove into alignment with the upper edge of the panel opening. Expansion of the resilient member raises the housing within the opening to cause the upper groove to engage the upper edge of the panel opening for firmly securing the control station housing to the panel. A screw threadably received in an opening in the housing may be subsequently adjusted to extend into the lower groove within the panel opening to prevent compression, excessive of the resilient member which might permit the upper groove of the housing to disengage from the upper edge of the opening. The housing further comprises a peripheral flange against which a flat gasket is mounted for compression against a rear surface of the panel, and the resilient member in the lower groove comprises a protrusion formed on the rubber gasket.

The invention and its advantage may be more fully understood when reading the following description and claims in conjunction with the accompanying drawings.

BRIEF DESCRIPTION OF THE DRAWINGS

FIG. 1 is a front elevational view of a control station housing constructed in accordance with this invention;

FIG. 2 is a sectional view of a panel showing an opening in the panel and showing in side elevation the control station housing of this invention as it is being inserted into the panel opening;

FIG. 3 is a sectional view of a panel showing an opening in the panel and showing in side elevation the control station housing of this invention in its fully assembled position with respect to the panel;

DESCRIPTION OF THE PREFERRED EMBODIMENT

The control station of this invention comprises a rectangular box-like housing 2 shown in front elevation in FIG. 1. Housing 2 comprises a forwardly projecting body comprising front wall $2a$, side walls $2b$, upper wall $2c$, lower wall $2d$, a pair of ribs $2e$ and a short vertical wall $2f$. A planar front surface of front wall $2a$ is recessed from the forward edges of side walls $2b$, upper wall $2c$ and lower wall $2d$. Side walls $2b$ and lower wall $2d$ project directly rearward at essentially right angles to the planar front surface of wall $2a$, while upper wall $2c$ projects angularly upward in the rearward direction. The lower extremities of side walls $2b$ form a pair of triangular ribs $2e$ adjacent the lower wall $2d$. Ribs $2e$ join with a short vertical rear wall $2f$ extending downwardly from lower wall $2d$. A peripheral flange $2g$ projects outwardly along the rear edge of housing 2, the lower transverse edge of flange $2g$ being offset rearwardly at $2h$. As seen best in FIGS. 2 and 3, a groove $2j$ is formed in the exterior surface of upper wall $2c$ at the juncture of that surface with flange $2g$. A similar groove $2k$ is formed in a lower surface of the housing at the juncture of lower wall $2d$ with flange $2g$, the forward edge of the groove $2k$ being formed by the rear surface of vertical wall $2f$. Housing 2 is open to the rear. A vertically disposed central rib $2m$ extends between interior surfaces of the upper wall $2c$ and the lower wall $2d$. Planar front surface $2a$ is provided with a plurality of knockouts $2n$, each consisting of a pair of concentric shallow grooves on both the front and rear surfaces of the planar front wall. In a manner well known in the art, the knockouts $2n$ may be removed as desired and one-hole mounting pilot control devices such as pushbutton switches, selector switches, indicator lights or the like may be individually affixed to the planar surface $2a$ within respective knockouts $2n$. A circular boss $2p$ is formed on the rear of housing 2 adjacent the lower wall $2d$; the boss $2p$ being centrally located with respect to the width, or transverse dimension of the housing. Boss $2p$ has an opening $2q$ therein, which extends through flange $2g$ to communicate with lower groove $2k$. The flange 2g is also provided with a pair of hooks 2r molded on the rear surface at the upper end of the flange.

Figure 4:
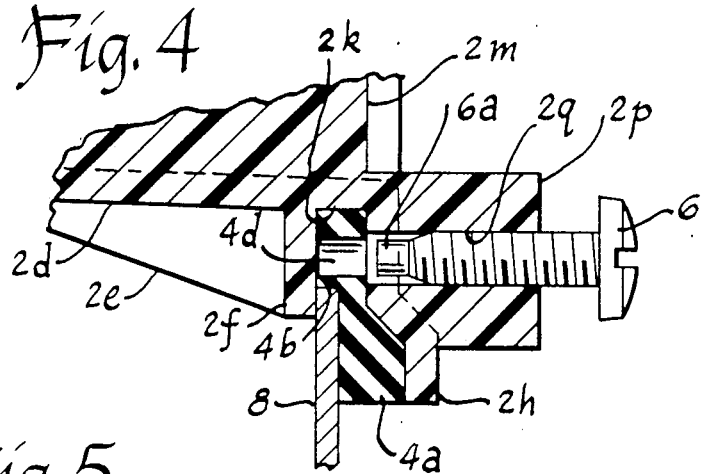
FIG. 4 is a fragmentary sectional view showing a retaining feature of the control station housing of this invention in a released position.
Figure 5:
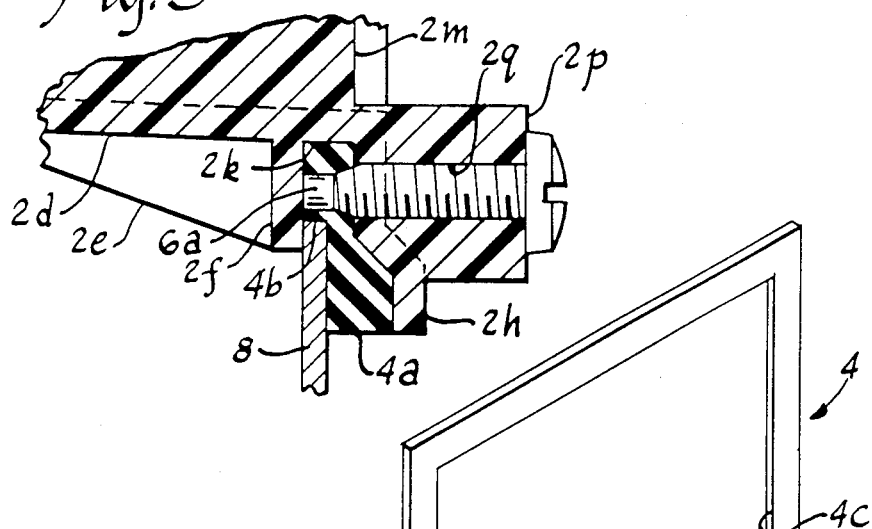
FIG. 5 is a view similar to FIG. 4 but showing the retaining feature in an engaged position.
Figure 6:
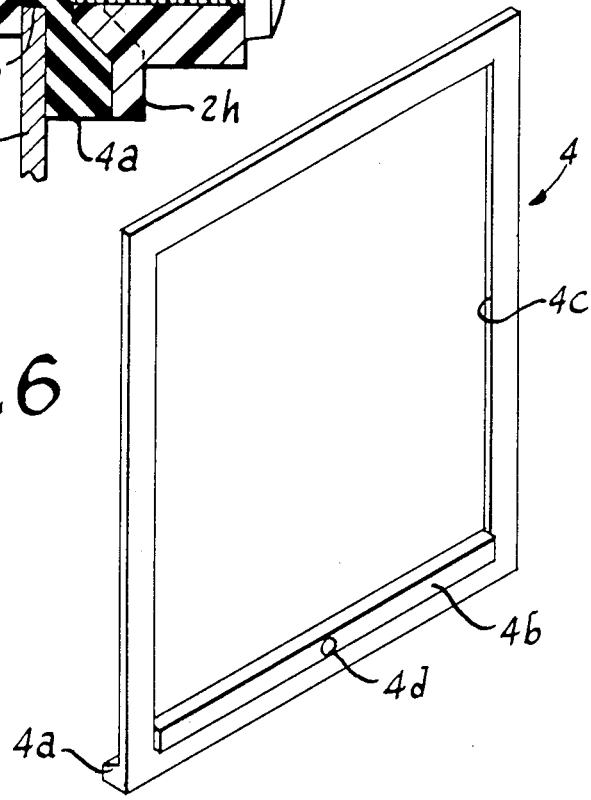
FIG. 6 is an isometric view of a gasket utilized in conjunction with the control station housing of this invention.

A flat rectangular rubber gasket 4 (shown separately in FIG. 6) is disposed over housing 2 and positioned against the forward flat surface of flange 2g. The lower transverse leg of gasket 4 comprises a web 4a of increased thickness projecting in the rearward direction, the configuration of web 4a being essentially complemental to the offset 2h of housing 2. A rectangular protrusion 4b in the shape of a rectangular strip is formed on the lower transverse leg of gasket 4 opposite web 4a and along the transverse length of the lower edge of a rectangular opening 4c. An aperture 4d is provided in protrusion 4b at the midpoint of the transverse length of the protrusion. When the gasket 4 is placed against flange 2g of housing 2, the protrusion 4b fills the bottom portion of lower groove 2k and the aperture 4d aligns with hole 2q in housing 2.

A screw 6 is threadably inserted into hole 2q of the boss 2p. The end of the threaded shank of screw 6 is provided with a cylindrical tip 6a which has a diameter corresponding to the diameter of aperture 4d.

As seen best in FIG. 2, the control station comprising housing 2 and any electrical pilot control devices mounted thereto (not shown) may be assembled to a panel 8. As used herein, "panel" is intended to mean any relatively flat sheet-like member such as a wall of an enclosure, a separate mounting plate or the planar area of a door such as, in this exemplary embodiment, the door of a motor control center or the like. The panel 8 is substantially vertically oriented and has a rectangular opening therein corresponding to the peripheral shape of the box-like body portion of housing 2 comprising walls 2b, 2c and 2d. The vertical dimension of the panel opening is greater than the vertical dimension between the respective bottoms of grooves 2j, 2k. However, the vertical dimension between the outer forward edge of upper groove 2j and a corresponding edge of lower groove 2k is greater than the vertical dimension of the panel opening so that the forward vertical surfaces of the grooves 2j and 2k of housing 2 may firmly seat against the front surface of the panel 8 at the upper and lower edges of the panel opening. The outer dimensions of flange 2g are considerably larger than the panel opening in both vertical and transverse directions to provide a wide stop surface for seating against the rear surface of the panel 8.

The control station housing 2 is assembled to the panel 8 by annularly inserting the lower end through the panel opening from the rear surface of the panel, engaging the groove 2k over the lower edge of the panel opening. In this position, the lower edge of the panel opening engages the lower side of resilient protrusion 4b. At the same time, the transverse thickness of web 4a is compressed against the rear side of the panel 8 by the tilted disposition of the housing 2 with respect to the panel. By urging the housing 2 downwardly, protrusion 4b is resiliently compressed against the bottom of groove 2k to enable the upper end of the housing 2 to be pivoted forwardly whereby the uppermost portion of the exterior surface of wall 2c moves forwardly through the panel opening until the flat forward surface of gasket 4 which is backed by stop flange 2g engages the rear surface of panel 8. Forward pressure on the rear of housing 2 compresses the gasket 4 between the panel 8 and flange 2g to cause the upper groove 2j to become aligned with the panel at the upper edge of the panel opening whereupon the bias provided by compressed protrusion 4b urges the housing 2 upwardly and the groove 2j into engagement with the upper edge of panel opening to firmly lock the housing 2 to the panel 8 within the opening.

To prevent the weight of the control station from compressing the protrusion 4b or from causing it to deteriorate and the housing 2 to become offset downwardly through prolonged use, screw 6 is threadably advanced after the aforedescribed attachment of the housing 2 to the panel 8 such that the tip 6a extends into the lower groove 2k and into the aperture 4d of gasket 4. The tip 6a of screw 6 is thus firmly disposed within the opening of panel 8 with only a thin web of gasket material between the tip 6a and the lower edge of the panel opening. Therefore the weight of the control station is borne by the tip 6a of screw 6 engaging the lower edge of the panel opening, preventing the resilient protrusion 4b from compressing or permanently deforming, which would cause the control station housing 2 to move lower within the panel opening such that the upper groove 2j could become disengaged from the upper edge of the panel opening.

When it is desired to remove the motor control unit for maintenance, service or any other reason, the control station may be readily removed from the door as follows: the screw 6 is backed outwardly of the hole 2q until the end 6a clears the groove 2k, whereupon the control station may be urged downwardly against the resilient bias of protrusion 4b to compress the latter until upper groove 2j disengages with the upper edge of the panel opening. The upper end of the housing is then tilted rearwardly of the panel and the control station may be removed from the opening without disconnecting any wiring between the pilot control devices mounted to the housing and the control apparatus. For convenience, the hooks 2r enable the control station to be hooked onto a cross brace or other structural formation of the removable motor control unit while the latter is being worked on.

While the foregoing has described a particular preferred embodiment of the control station of this invention, it is to be understood that it is susceptible of various modifications without departing from the scope of the appended claims.

I claim:

1. In a control station housing adapted for having electrical control apparatus mounted thereto comprising:

a substantially vertically oriented panel having an opening therein;

said housing having upper and lower transverse grooves open outwardly of said housing for receiving respective upper and lower edges of said panel opening, a vertical dimension between an outer edge of said upper groove and a corresponding edge of said lower groove being greater than a vertical dimension of said opening and a vertical dimension between bottoms of said respective grooves being less than said vertical dimension of said opening, said housing being insertable into said opening to engage said lower groove over said lower edge permitting rotation of an upper surface of said housing through said opening to align said upper groove with said upper edge;

resilient means in said lower groove biasing said housing upwardly to effect engagement of said upper groove with said upper edge; and means carried by said housing extendable into said lower groove within said panel opening preventing downward movement of said housing within said opening sufficient to permit disengagement between said upper groove and said upper edge.

2. The invention defined in claim 1 wherein said extendable means comprises a screw threadably received in a hole in said housing centrally located along a transverse dimension of said lower groove and opening into said lower groove.

3. The invention defined in claim 2 wherein said resilient means comprises a rubber strip disposed along the transverse length of said lower groove and having an aperture therein aligned with said hole in said housing.

4. The invention defined in claim 1 wherein said housing comprises outwardly extending stop means aligned with rear surfaces of said grooves abutting a rear surface of said panel.

5. The invention defined in claim 4 wherein said stop means comprises an outwardly projecting peripheral flange aligned with rear surfaces of said grooves abutting a rear surface of said panel around said opening.

6. The invention defined in claim 5 wherein a transverse lower edge of said flange is offset rearwardly permitting tilted insertion of said housing into said opening and engagement of said lower groove and said lower edge.

7. The invention defined in claim 6 wherein said resilient means comprises an elongated protrusion along a lower transverse portion of a continuous flat rubber gasket disposed against a forward face of said flange, said gasket being compressed between said flange and a rear surface of said panel.

8. The invention defined in claim 7 wherein said lower transverse portion of said gasket is enlarged rearwardly filling space between said offset flange and said panel.

9. The invention defined in claim 8 wherein said enlarged lower transverse portion of said gasket is compressed upon tilted insertion of said housing into said panel opening.

10. The invention defined in claim 7 wherein said extendable means comprises a screw threadably received in a hole in said housing centrally located along a transverse dimension of said lower groove and opening into said groove; and said elongated protrusion of said gasket comprises an aperture aligned with said hole in said housing.

11. The invention defined in claim 10 wherein said aperture is located near a lower edge of said protrusion.

12. The invention defined in claim 4 further comprising a pair of rearwardly extending downwardly open hooks depending from said housing for hanging said control station housing on a transversely extending structure.

13. The invention defined in claim 1 wherein said panel comprises a substantially planar portion of a door for an enclosure.

14. In a control station housing adapted for having electrical control apparatus mounted thereto comprising:

a substantially vertically oriented panel having an opening therein;

said housing comprising a forwardly projecting body and a peripheral flange projecting outwardly from said body, upper and lower transverse grooves at a juncture of said body and said flange, said grooves being wider than the thickness of said panel and open upwardly and downwardly, respectively, a vertical dimension between an outer forward edge of said upper groove and a corresponding edge of said lower groove being greater than a vertical dimension of said panel opening, a vertical dimension between bottoms of said respective grooves being less than said vertical dimension of said panel opening, and said flange being larger than said panel opening for overlapping said panel around a periphery of said opening;

a flat gasket of resilient material disposed against said flange, said gasket comprising a protrusion along a lower transverse leg, said protrusion extending into said lower groove;

a screw carried by said housing advancable to extend into said lower groove;

said housing being mounted to said panel by:

(i) inserting a lower portion of said housing body through said panel opening;

(ii) engaging said lower groove over a lower edge of said panel opening;

(iii) pressing said housing downwardly for compressing said protrusion;

(iv) pivoting an upper end of said housing body through said panel opening until said flange engages a rear surface of said panel with said gasket interposed said panel and said flange;

(v) releasing downward pressure on said housing, thereby permitting said protrusion to restore to a non-compressed condition biasing said housing upwardly in said opening for effecting engagement of said upper groove with an upper edge of said panel opening; and (vi) advancing said screw into said lower groove, said screw extending transversely across said lower edge of said panel opening in interference therewith, preventing said housing from moving downwardly in said panel opening sufficiently to effect disengagement between said upper groove and said upper edge.

* * * * *